United States Patent
Maas et al.

(10) Patent No.: US 11,213,189 B2
(45) Date of Patent: Jan. 4, 2022

(54) ENDOSCOPIC DEVICE AND METHOD FOR ENDOSCOPIC EXAMINATION

(71) Applicant: Aesculap AG, Tuttlingen (DE)

(72) Inventors: Hans-Gerd Maas, Dresden (DE); Niklas Paul Conen, Meppen (DE); Thomas Luhmann, Wardenburg (DE)

(73) Assignee: Aesculap AG, Tuttlingen (DE)

( * ) Notice: Subject to any disclaimer, the term of this patent is extended or adjusted under 35 U.S.C. 154(b) by 350 days.

(21) Appl. No.: 16/244,187

(22) Filed: Jan. 10, 2019

(65) Prior Publication Data

US 2019/0142250 A1 May 16, 2019

Related U.S. Application Data

(63) Continuation of application No. PCT/EP2017/067195, filed on Jul. 10, 2017.

(30) Foreign Application Priority Data

Jul. 14, 2016 (DE) ..................... 10 2016 113 000.1

(51) Int. Cl.
*A61B 1/00* (2006.01)
*A61B 1/07* (2006.01)
(Continued)

(52) U.S. Cl.
CPC ........ *A61B 1/00193* (2013.01); *A61B 1/0005* (2013.01); *A61B 1/005* (2013.01);
(Continued)

(58) Field of Classification Search
CPC ............ A61B 1/00193; A61B 1/00071; A61B 1/3132; A61B 1/0638; A61B 1/0005;
(Continued)

(56) References Cited

U.S. PATENT DOCUMENTS 5,836,869 A * 11/1998 Kudo ..................... A61B 90/92
600/173
8,262,559 B2   9/2012 Krattiger
(Continued)

FOREIGN PATENT DOCUMENTS

DE   102008018636   10/2009
DE   102009046108    5/2011
(Continued)

OTHER PUBLICATIONS

Gandhi et al., "High-Resolution Depth Maps Based on TOF-Stereo Fusion", ICRA 2012—IEEE International Conference on Robotics and Automation, May 2012, 9 pages.
(Continued)

*Primary Examiner* — Aaron B Fairchild
(74) *Attorney, Agent, or Firm* — Lipsitz & McAllister, LLC

(57) ABSTRACT

The invention relates to an endoscopic device, in particular for medical applications, comprising an endoscope with a shaft that is introducible into a subject under examination, and a data processing unit, three or more optical imaging units having respective imaging elements arranged distally on the shaft and image sensors associated therewith for providing image data sets for the data processing unit, wherein the data processing unit is configured and programmed such that it uses the image data sets to determine corresponding image points therein and generates a 3D surface data set of an object imaged by the imaging units in the subject under examination. Moreover, the invention relates to a method for endoscopic examination.

20 Claims, 5 Drawing Sheets

(51) Int. Cl.
*A61B 1/06* (2006.01)
*G02B 23/24* (2006.01)
*A61B 1/313* (2006.01)
*A61B 1/005* (2006.01)
*A61B 1/05* (2006.01)

(52) U.S. Cl.
CPC ...... *A61B 1/00059* (2013.01); *A61B 1/00071* (2013.01); *A61B 1/00087* (2013.01); *A61B 1/051* (2013.01); *A61B 1/0615* (2013.01); *A61B 1/0638* (2013.01); *A61B 1/07* (2013.01); *A61B 1/3132* (2013.01); *G02B 23/2415* (2013.01); *G02B 23/2476* (2013.01); *A61B 1/05* (2013.01)

(58) Field of Classification Search
CPC . A61B 1/00059; A61B 1/00087; A61B 1/005; A61B 1/051; A61B 1/0615; A61B 1/07; A61B 1/05; A61B 1/0051; G02B 23/2415; G02B 23/2476
See application file for complete search history.

(56) References Cited

U.S. PATENT DOCUMENTS

| | | | |
|---|---|---|---|
| 8,929,645 B2 | 1/2015 | Coffman | |
| 9,939,349 B2 | 4/2018 | Mueller et al. | |
| 2001/0031912 A1 | 10/2001 | Adler | |
| 2002/0054208 A1* | 5/2002 | Goldstein | H04N 13/257 348/59 |
| 2002/0071616 A1 | 6/2002 | Yoshida | |
| 2002/0114071 A1 | 8/2002 | Igarashi | |
| 2004/0019274 A1 | 1/2004 | Galloway, Jr. et al. | |
| 2004/0023612 A1 | 2/2004 | Kriesel | |
| 2007/0197875 A1* | 8/2007 | Osaka | A61B 1/04 600/173 |
| 2009/0259098 A1 | 10/2009 | Krattinger | |
| 2009/0268010 A1 | 10/2009 | Zhao et al. | |
| 2010/0130869 A1 | 5/2010 | Hauger et al. | |
| 2011/0306832 A1* | 12/2011 | Bassan | A61B 1/00096 600/109 |
| 2012/0249741 A1* | 10/2012 | Maciocci | G06T 15/503 348/46 |
| 2013/0258067 A1 | 10/2013 | Zhang et al. | |
| 2013/0331648 A1* | 12/2013 | Jacobsen | A61B 1/00179 600/109 |
| 2014/0024951 A1 | 1/2014 | Herzlinger et al. | |
| 2014/0153816 A1 | 6/2014 | Cohen et al. | |
| 2014/0375784 A1 | 12/2014 | Massetti | |
| 2015/0046818 A1 | 2/2015 | Wade | |
| 2015/0077519 A1 | 3/2015 | Scott et al. | |
| 2015/0085072 A1 | 3/2015 | Yan et al. | |
| 2015/0359418 A1 | 12/2015 | Feussner et al. | |
| 2016/0249988 A1 | 9/2016 | Pfeifer et al. | |
| 2016/0374764 A1 | 12/2016 | Kemp et al. | |
| 2017/0209222 A1 | 7/2017 | Gassner et al. | |

FOREIGN PATENT DOCUMENTS

| | | | | |
|---|---|---|---|---|
| DE | 102010041870 | | 4/2012 | |
| DE | 102011087357 | | 5/2013 | |
| DE | 102011084920 | | 3/2014 | |
| DE | 102013200898 | | 7/2014 | |
| DE | 102013112375 | | 5/2015 | |
| DE | 102014104800 | | 10/2015 | |
| JP | 2004320722 | | 11/2004 | |
| JP | 2005087468 | | 4/2005 | |
| JP | 2011100426 | | 5/2011 | |
| WO | 2006005061 | | 1/2006 | |
| WO | 2011020505 | | 2/2011 | |
| WO | 2013045108 | | 4/2013 | |
| WO | WO-2014061428 A1 * | 4/2014 | ......... A61B 1/00006 |

OTHER PUBLICATIONS

Hansard et al., "Time of Flight Cameras: Principles, Methods, and Applications", SpringerBriefs in Computer Science, Nov. 2012, 103 pages.

Zhu et al., "Fusion of Time-of-Flight Depth and Stereo for High Accuracy Depth Maps", 2008 IEEE Conference on Computer Vision and Pattern Recognition, Jun. 2008, 8 pages.

Groch et al.; "In-vitro Evaluation von endoskopischer Oberflächenrekonstruktion mittels Time-of-Flight-Kameratechnik", Workshop—Bildverarbeitung für die Medizin, Lübeck, 2011, p. 184-188.

Heinrichs, Matthias, "Automatische Generierung von 3D-Modellen mittels Sequenzen hochauflösender Bildtripel", PhD Thesis, TU Berlin, 2011, 114 pages.

Heinrichs et al., "Efficient Semi-Global Matching for Trinocular Stereo", International Archives of Photogrammetry, Remote Sensing and Spatial Information Sciences, vol. 36, 2007, 6 pages.

Maas, Hans-Gerd, "Digital Photogrammetry in Threedimenstional Flow Measurement Technique", PhD Thesis, ETH Zurich, 1992, 159 pages.

Mayer, Helmut, "Robust Orientation, Calibration, and Disparity Estimation of Image Triplets", Institute for Photogrammetry and Cartography, Bundeswehr University Munich, 2003, 8 pages.

Mayer, Helmut, "Estimation of and View Synthesis With the Trifocal Tensor", Institute for Photogrammetry and Cartography, Bundeswehr University Munich, 2002, 7 pages.

* cited by examiner

ENDOSCOPIC DEVICE AND METHOD FOR ENDOSCOPIC EXAMINATION

CROSS-REFERENCE TO RELATED APPLICATIONS

This application is a continuation patent application of international application number PCT/EP2017/067195, filed on Jul. 10, 2017, and claims the benefit of German application number 10 2016 113 000.1, filed Jul. 14, 2016, which are incorporated herein by reference in their entirety and for all purposes.

FIELD OF THE INVENTION

The present invention relates to an imaging endoscopic device, in particular for medical applications, comprising an endoscope with a shaft that is introducible into a subject under examination, and a data processing unit, and optical imaging units for providing image data sets for the data processing unit.

Moreover, the present invention relates to a method for the endoscopic examination of a subject under examination, in particular for medical applications, in which a shaft of an endoscope is introduced into a subject under examination and an object in the subject under examination is imaged, wherein image data sets are provided to a data processing unit.

BACKGROUND OF THE INVENTION

The present invention is described below in particular with reference to a medical application, but is not restricted to this area of application. Endoscopic examinations may for example also be carried out in the context of the manufacture or maintenance of industrial articles. An example of application in this regard is the endoscopic examination of gas turbines, as described in WO 2013/045108 A1.

In medical applications, the shaft of the endoscope is introduced into the (human or animal) body as the subject under examination in order to image objects such as internal organs in cavities, assisting the surgical procedure. It is also possible to image surgical instruments used by the surgeon during the procedure. In this context, the use of stereo endoscopes to provide a spatial representation of an object to the surgeon is known.

WO 2006/005061 A2 describes a device in which three optical imaging units are used. Using two imaging units, a stereo image can be displayed to the surgeon at a display unit. It is further possible to generate an additional image using a third imaging unit and to represent it for example as an insert in the stereo image in order to provide the surgeon with additional information.

An object underlying the present invention is to provide an endoscopic device and a method for endoscopic examination by which additional information can be obtained for the purpose of a more comprehensive examination of the subject under examination.

SUMMARY OF THE INVENTION

In a first aspect of the invention, an endoscopic device, in particular for medical applications, is provided, comprising an endoscope with a shaft that is introducible into a subject under examination, and a data processing unit, three or more optical imaging units having respective imaging elements arranged distally on the shaft and image sensors associated therewith for providing image data sets for the data processing unit. The data processing unit is configured and programmed such that it uses the image data sets to determine corresponding image points therein and generates a 3D surface data set of an object imaged by the imaging units in the subject under examination.

In a second aspect of the invention, a method for the endoscopic examination of a subject under examination, in particular for medical applications, is provided, in which a shaft of an endoscope is introduced into a subject under examination and an object in the subject under examination is imaged. Three or more optical imaging units having respective imaging elements that are arranged distally on the shaft and image sensors associated therewith are provided for the purpose of providing image data sets for the data processing unit. The data processing unit uses the image data sets to determine corresponding image points therein and generates a 3D surface data set of the object imaged by the imaging units.

BRIEF DESCRIPTION OF THE DRAWINGS

The foregoing summary and the following description may be better understood in conjunction with the drawing figures, of which.

DETAILED DESCRIPTION OF PREFERRED EMBODIMENTS OF THE INVENTION

Figure 1:
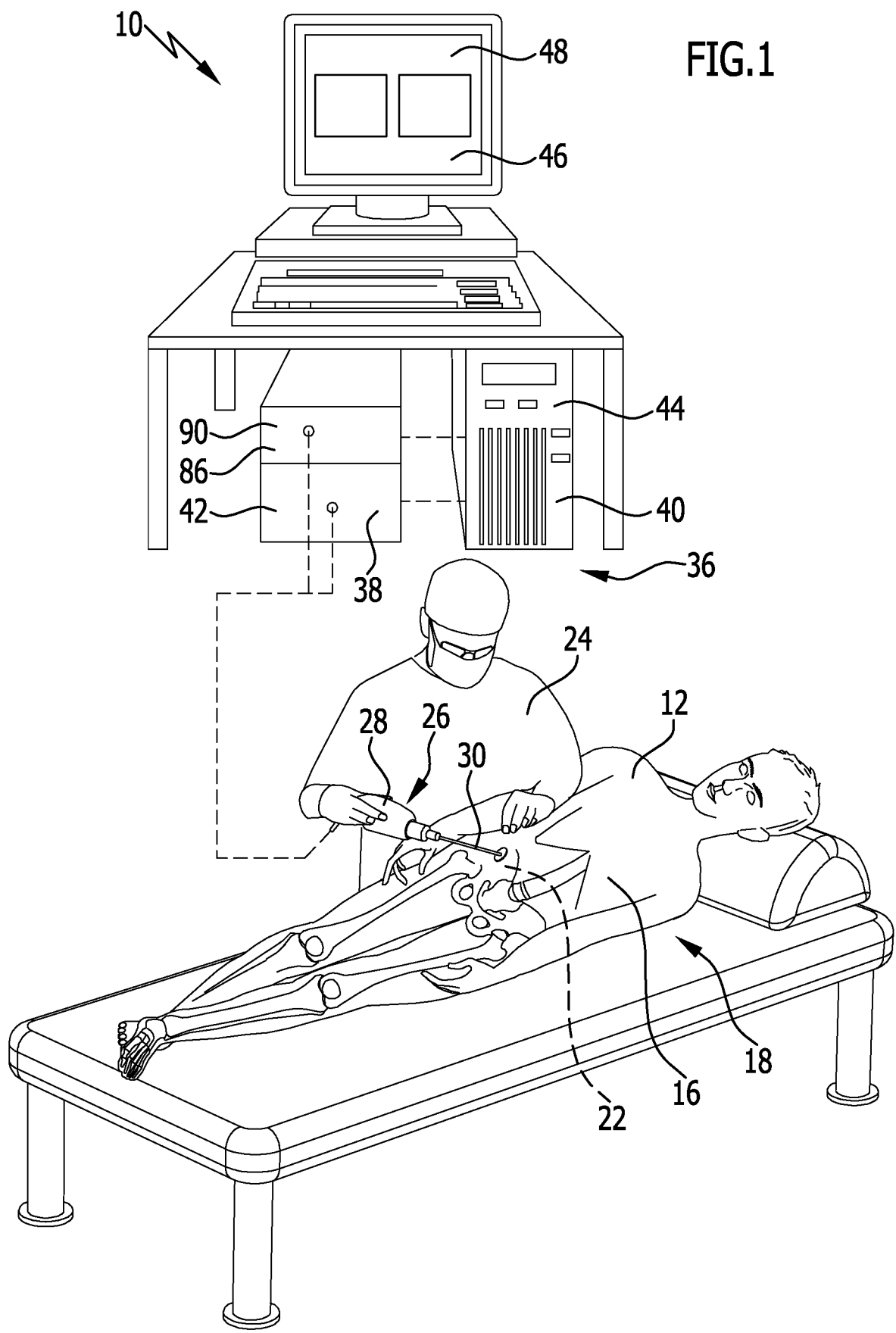
FIG. 1 shows an endoscopic device in accordance with the invention for a medical application on a patient by a surgeon.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to an endoscopic device, in particular for medical applications, comprising an endoscope with a shaft that is introducible into a subject under examination, and a data processing unit, three or more optical imaging units having respective imaging elements arranged distally on the shaft and image sensors associated therewith for providing image data sets for the data processing unit. The data processing unit is configured and programmed such that it uses the image data sets to determine corresponding image points therein and generates a 3D surface data set of an object imaged by the imaging units in the subject under examination.

In the device in accordance with the invention, it is provided for at least three imaging units to be used, wherein in an advantageous embodiment it is also possible to provide four or more imaging units. Arranged distally on the shaft are imaging elements in the field of view whereof there is located an object for imaging. Light focused by the imaging elements can be transmitted to the image sensors, which may be arranged in the shaft or in a housing positioned outside the subject under examination. The data processing unit examines the image data sets for corresponding (so-called homologous) image points, wherein the image data sets of three or more image sensors, preferably of all the image sensors, are taken into account. In contrast to devices known from the prior art, in accordance with the invention there is the possibility that a 3D reconstruction of the observed scene is possible. By providing three or more image data sets, any ambiguities and inaccuracies that, as is known, may occur during the evaluation of stereo image data sets can be largely eliminated. Using the device, it is hence possible to generate a 3D surface data set of imaged objects that is characterized by greater accuracy. The 3D surface data set can be used as the basis for further endoscopic examination and is taken into account for example for detecting as a function of time a change in the position and/or shape of one or more objects, a point that is discussed in more detail below.

The device in accordance with the invention is particularly suitable for medical endoscopic examinations. These examinations are faced with the challenge that endoscopic devices must be compact in order to keep invasiveness for the patient as low as possible (for example, any additional incisions are to be avoided), in particular taking into account the restricted spatial conditions inside the body. When detecting, reconstructing and identifying endogenous structures, the fact that they are predominantly lacking in texture and so have only few structural properties that are simple to analyze using image processing technology proves particularly difficult. Another cause of difficulty is the fact that there are reflections from endogenous structures as a result of their lack of a marked structure and fluid adhering to them such as water or blood, and these reflections can only be analyzed in the image data sets with difficulty. Here, a particular cause of intrinsically undesirable reflections is illumination in the interior of the body, which is nonetheless necessary. Moreover, because of the spatial constraints, in practice there is the problem that imaging elements with large apertures are used, and these give rise to distortions in the image data sets and allow only a small depth of field, also caused by the small base distance between the imaging elements distally on the shaft. By utilizing at least three image data sets, the present invention makes it possible to eliminate ambiguities to a considerable extent and hence to obtain information on the imaged objects that is more reliable overall.

The 3D surface data set may be generated from a so-called "point cloud" made up of a finite number of points, or comprises a finite number of points of this kind determined from the identified corresponding image points.

For the purpose of identifying and determining corresponding image points in the three or more image data sets, those skilled in the art can make use of algorithms known to them for multi-image matching, for example by the core line intersection method.

It is favorable if the data processing unit determines the corresponding image points for generating the 3D data set in real time, for example at intervals of a few seconds, preferably in the millisecond range. If the 3D surface data set is displayed on a display unit, an object can thus be represented in real time to a certain extent.

Advantageously, changes in the position and/or shape of the object are determinable by the device as a function of time. This should in particular be understood to mean that the object can be tracked, at least partly. A movement of the object with a change in location and/or orientation and/or a change in shape of one or more objects can be determined by the data processing unit in that successive 3D data sets differ from one another, wherein the object or objects can (preferably simultaneously) be identified in each case in the 3D data sets and hence tracked as a function of time. This produces a major benefit for the user. In the context of medical endoscopy, it allows pulsating organs for example to be identified and tracked.

It may be provided for the data processing unit to use two image data sets to generate a stereo image data set, which is examined for corresponding image points in at least one further image data set.

Further, it may be provided for a respective two image data sets to be combined with one another stereoscopically and compared with a further image data set. Accordingly, in a preferred embodiment it is advantageous if the data processing unit generates from each two image data sets a stereo image data set, which is examined for corresponding image points in a respective further image data set.

It may be provided for the device to comprise a display unit coupled to the data processing unit.

It is favorable if the data processing unit uses two image data sets to generate a stereo image of the object and represents it on the display unit. It is possible to display to the user—for example the surgeon—an intuitively understandable stereo image for the purpose of guiding the endoscope inside the subject under examination.

As an alternative or in addition, it is favorable if the data processing unit represents an image of the 3D data set on the display unit in particular as a function of time. The 3D (surface) data set that is generated by the data processing unit with the object reconstructed from the image information can give the user valuable additional information during the endoscopic procedure. Displays in artificial colors are possible, to emphasize interesting properties of the object. Advantageously, it is possible for the user to navigate within the represented 3D data set in order to be able to view the object from different sides without having to guide the endoscope for this purpose.

In an advantageous embodiment, the imaging elements can be arranged collinearly on the shaft. In a plan view of the distal end of the shaft, the imaging elements may be positioned lying next to one another, for example equidistantly. Respective axes defined by the imaging elements are in this case arranged along a straight line running through them and/or are oriented in pairs parallel to one another.

In a different kind of advantageous embodiment, it is favorable if one of the imaging elements is arranged on the shaft symmetrically in relation to a base formed by two further other imaging elements. For example, two imaging elements form a base of a stereoscopic system, wherein a third imaging element is positioned symmetrically in relation to the base.

Favorably, the imaging elements, in particular in the advantageous last-named embodiment, are arranged in a regular arrangement on the shaft, for example in an isosceles and in particular equilateral triangle, in each case in relation to a plan view of the shaft in the proximal direction. With a regular arrangement of the imaging elements, for example three imaging elements, in an equilateral triangle, it is possible to achieve as compact as possible a construction of the endoscope.

It proves favorable if at least two imaging elements are arranged in a planar arrangement with one another. In the present document, those skilled in the art may understand by this in particular that optical axes of the imaging elements are oriented parallel to one another. Optical planes of the imaging elements, in particular the planes of lenses, preferably coincide.

As an alternative or in addition, it may be provided for at least two image sensors to be arranged in a planar arrangement with one another. In the present document, this may be understood in particular to mean that planes formed by the image sensors may coincide or be arranged parallel to one another.

In an advantageous embodiment, it is provided for all the imaging elements and/or all the image sensors respectively to be arranged in a planar arrangement with one another.

The optical imaging properties of the imaging elements (aperture, focal length, etc.) are preferably identical. The imaging properties of the imaging units as a whole may be identical.

In an advantageous embodiment, it is favorable if the image sensors are arranged in the shaft and are coupled by way of signal lines to the data processing unit, which is positioned outside the subject under examination. In particular, there is the possibility of providing a so-called "chip on the tip" endoscope.

In a different kind of advantageous embodiment, it is provided for the imaging elements to be coupled, by way of light conducting elements guided in the shaft, to the image sensors, which are arranged in a housing, outside the subject under examination. Objects are imaged by way of the imaging elements into the light conducting elements, and by way of these are sent to the image sensors arranged outside the subject under examination.

It proves favorable if the device comprises an illuminating unit having at least one illuminating element that is introducible into the subject under examination. This provides the possibility of illuminating the scene and generating superior-quality images of objects.

Advantageously, a plurality of illuminating elements is provided. The illuminating elements may preferably be freely positionable in relation to one another and/or may favorably be activatable or deactivatable independently of one another so that the device is usable with as much versatility as possible for the person operating it.

Preferably, an illuminating element is associated with each imaging unit, wherein the number of illuminating elements may be the same as the number of imaging units.

It is favorable if the illuminating element comprises or forms at least one light conductor guided in the shaft. The fact that the light conductor is integrated in the shaft makes it possible to dispense with an illuminating element that is introducible into the subject under examination in addition to the shaft. This simplifies manipulation of the device for the person operating it in that an action on the endoscope simultaneously moves the light conductor. If the light conductor is adapted for an advantageous illumination of the field of view of the imaging elements, as a result a high quality of optical imaging can be achieved. The light conductor is or comprises for example a bundle of optical fibers guided in the shaft.

If there is a plurality of light conductors, it is preferably provided for the light conductors to be arranged symmetrically to one another and/or symmetrically in relation to the imaging elements in the shaft and in particular distally on the shaft, as seen in plan view. Here, it is desirable for illumination of the field of view of the imaging elements to be as homogeneous as possible.

For the purpose of minimizing reflections, the light conductors may advantageously be arranged radially to the outside of the imaging elements in relation to an axis of the shaft. In the present document, this may in particular be understood to mean that the light conductors are spaced radially further away from the shaft axis than axes of the imaging elements.

The shaft may be rigid or flexible. In the case of a flexible shaft, it may be provided for the flexible nature of the shaft to be rigidized.

Different configurations of the image sensors that may be present in different embodiments are discussed below. In principle, it is conceivable to replace image sensors, in which case the arrangement thereof in a housing arranged outside the subject under examination, as explained above, may be advantageous.

It may be provided for at least two of the three or more image sensors to differ from one another in respect of their spectral sensitivity and/or resolution.

For example, the spectral sensitivity of at least one image sensor may lie in the infrared range, the range of the visible spectrum, or the ultraviolet range. As a result of using IR or UV compatible image sensors, the person operating the device can be provided with information that is not available with conventional endoscopes having a sensitivity in the range of the visible spectrum, including stereo endoscopes.

In an advantageous implementation of the device, at least two of the three or more image sensors may have an identical configuration in respect of their spectral sensitivity and/or resolution.

For example, two image sensors are monochrome sensors for grayscales or for a color value (monochrome color). Two monochrome image sensors may for example be combined with a color image sensor (for example RGB). The image data sets of the monochrome sensors may be used for stereoscopic viewing at high resolution. For high-resolution three-dimensional color representations, the monochrome image data sets may be colored with the aid of the color image data set. Here, a pansharpening method may for example be employed. As an alternative or in addition, the color image data set may be utilized as a control image and/or for identifying outliers in the monochrome image data sets.

In a different kind of advantageous embodiment, there are provided for example two color image sensors (for example RGB), and a third image sensor whereof the spectral sensitivity is in another wavelength range, such as the infrared or the ultraviolet. A possible lower resolution of the image data sets in the other spectral range may be compensated with the color image data sets, for example using pansharpening.

As mentioned, two image sensors may be monochrome sensors and the third image sensor may be a color image sensor.

In a different kind of advantageous embodiment, it may be provided for at least one image sensor to be or to comprise a time-of-flight sensor that provides a distance image data set, and for the data processing unit to use the distance image data set to determine an item of distance information for the purpose of comparison with a stereo image data set obtained from other image data sets. This allows proximity values of surfaces from objects to be determined for the stereo matching.

It is favorable if, using the data processing unit, monitoring of the imaging properties of the imaging units is performable and, in the event of a discrepancy from a setpoint condition, an indication of this fact is preferably outputtable. The data processing unit may for example monitor corresponding image points as a function of time and hence perform to a certain extent continuous monitoring of the image data sets. This is advantageous if external factors or for example heating up of the endoscope results in a change in the orientation of the imaging units, and so the imaging properties change. If there is an indication, a person operating the device can be notified of this circumstance. As an alternative or in addition, it is favorable if the data processing unit can perform an automatic compensation of the changed imaging properties.

The device may have at least one tool for the purpose of manipulation in the subject under examination. The tool, for example a surgical instrument, favorably comprises a coding, which is detectable in the image data sets by the data processing unit for the purpose of identifying the tool. As a result, the tool may be tracked as a function of time, in particular as regards its position, for location and/or orientation. It is advantageous for the tool that is tracked in this way to be represented in a displayed 3D data set of an object, for the purpose of assisting the person operating the device during the procedure.

The present invention further relates to a method for the endoscopic examination of a subject under examination, in particular for medical applications, in which a shaft of an endoscope is introduced into a subject under examination and an object in the subject under examination is imaged, wherein three or more optical imaging units having respective imaging elements that are arranged distally on the shaft and image sensors associated therewith are provided for the purpose of providing image data sets for the data processing unit, wherein the data processing unit uses the image data sets to determine corresponding image points therein and generates a 3D surface data set of the object imaged by the imaging units.

The advantages that have already been mentioned in conjunction with the explanation of the device in accordance with the invention may likewise be achieved using the method. In this regard, the reader may be referred to the statements above. The method in accordance with the invention can preferably be performed using the device in accordance with the invention.

Advantageous exemplary embodiments of the method result from advantageous embodiments of the device, so in this regard too the reader may be referred to the explanations above.

Figure 2:
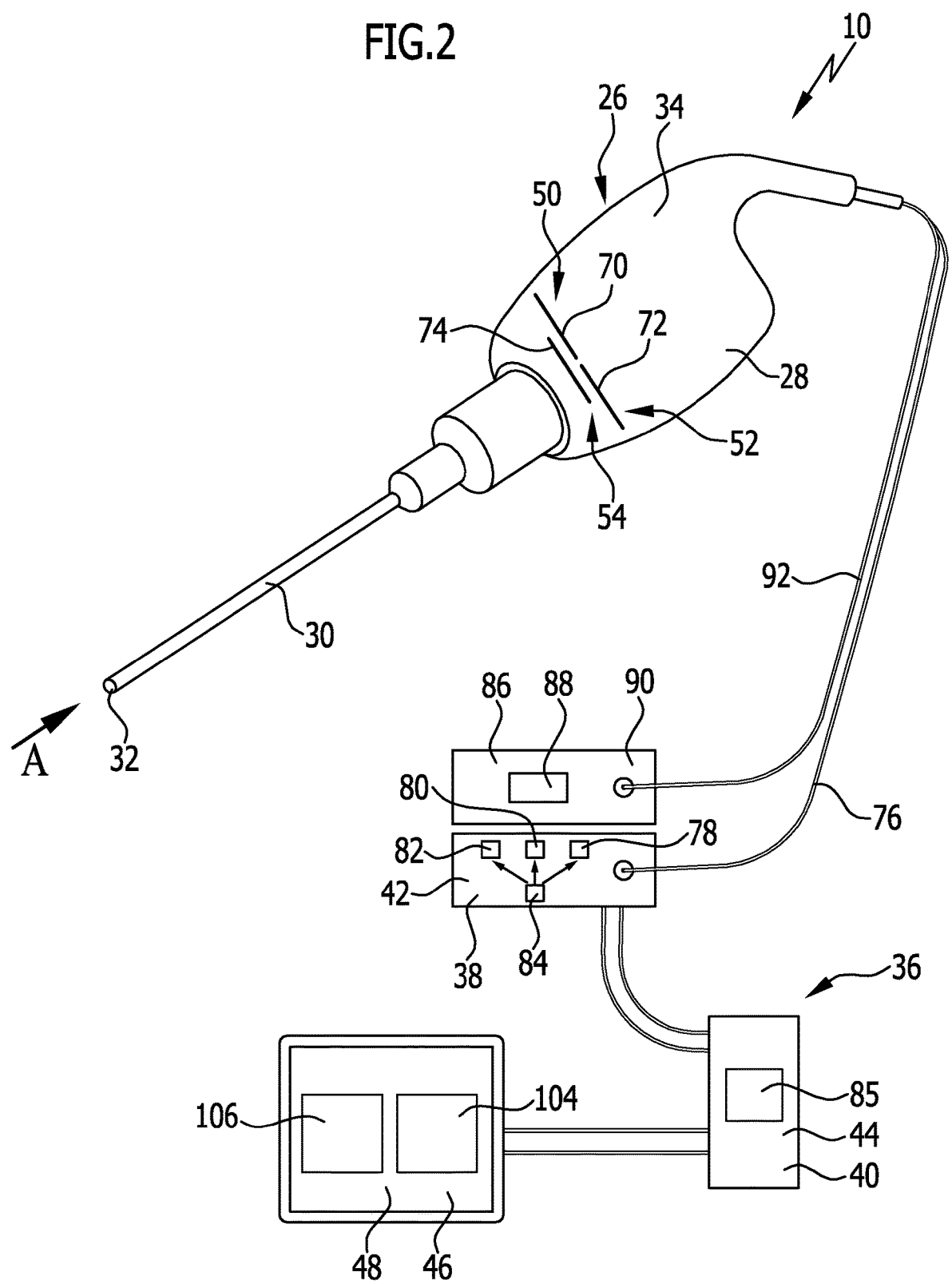
FIG. 2 shows in schematic form the device from FIG. 1.
Figure 5:
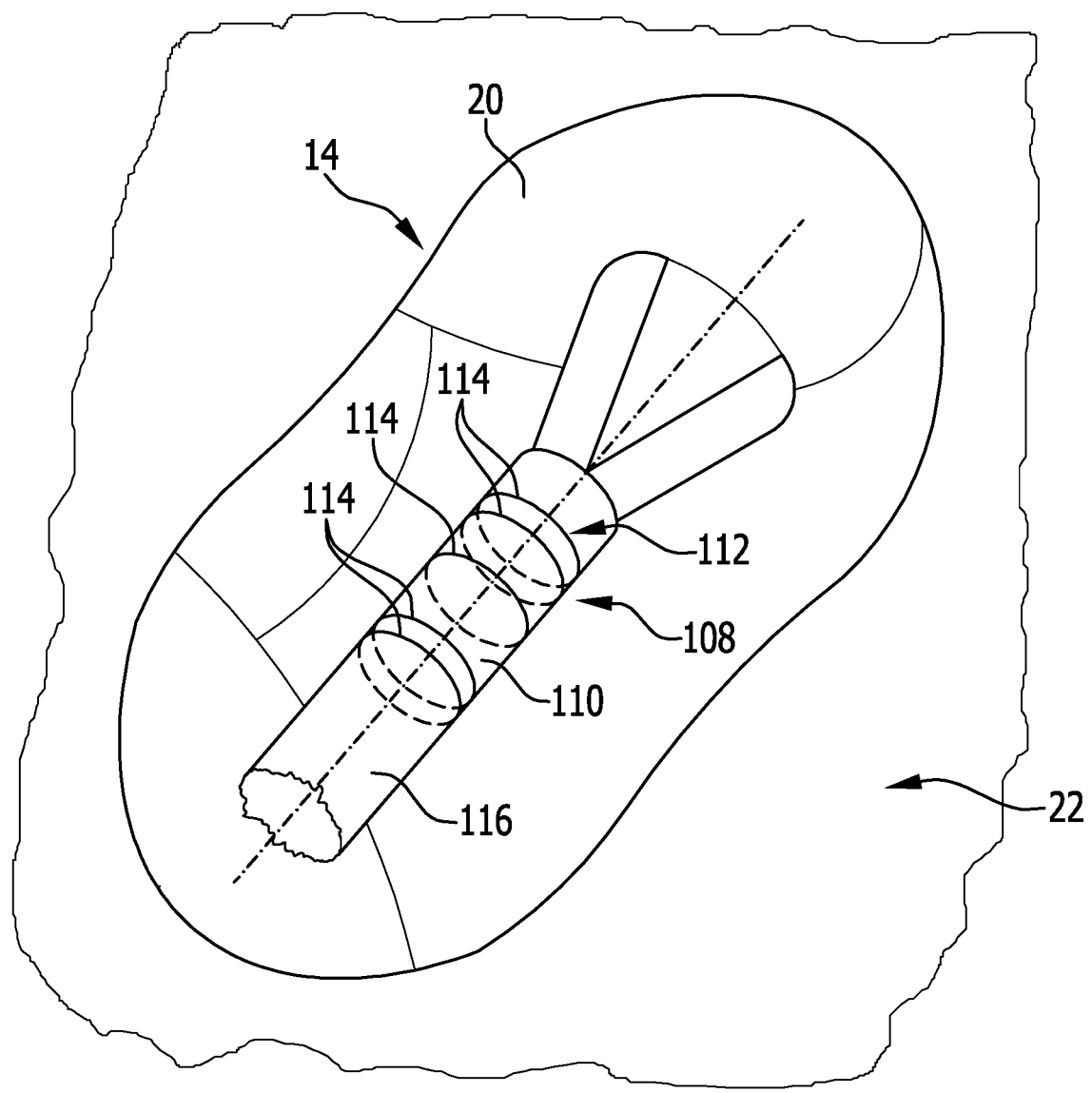
FIG. 5 shows a stereo image of a surgical instrument and an object (organ, or the like) in the body of a patient undergoing examination.

FIGS. 1 and 2 show in schematic form an advantageous embodiment, bearing the reference numeral 10, of an imaging endoscopic device in accordance with the invention. The device 10 is used for the endoscopic examination of a subject under examination 12 in order to examine objects therein, of which FIG. 5 shows an object 14 by way of example. A plurality of objects to be imaged may be provided and, in the present case, examined simultaneously.

Use of the device 10 is illustrated by way of the example of a surgical procedure, wherein the present invention is not restricted to medical applications. Endoscopic devices may for example also be used to monitor industrial devices during manufacture and maintenance.

As explained below, the device 10 comprises three imaging units. Other kinds of embodiments may comprise more than three imaging units, as already mentioned.

In the present exemplary application, the subject under examination 12 is accordingly the body 16 of a patient 18, and the object 14 is for example an organ 20 for examination, in the abdominal cavity 22. The person operating the device 10 is a surgeon 24.

The device 10 comprises an endoscope 26 that is guided manually by the surgeon 24 and has a handle element 28 and a shaft 30, which is held thereon and is at least partly introducible into the body 16. The shaft 30 has a distal end 32, which when the endoscope 26 is in use is arranged at the end remote from the surgeon 24. The handle element 28 comprises or forms a housing 34.

In the present case, the shaft 30 is configured to be rigid, but could also be flexible. As an alternative or in addition, it may be provided for the shaft 30 to be held on the handle element 28 such that its position is variable.

Further, the device 10 comprises a data processing unit 36, which in the present case comprises two constituent parts that are coupled to one another such that they may pass signals, and are arranged in housings 38, 40. An evaluation unit 42 of the data processing unit 36 is received in the housing 38, and a processor unit 44 is received in the housing 40. It goes without saying that it is also conceivable for the data processing unit 36 to have a common housing that receives both the evaluation unit 42 and the processor unit 44 coupled thereto.

The data processing unit 36 is coupled to a display unit 46 that comprises in particular an image display 48.

In the present document, the device 10 comprises three optical imaging units 50, 52 and 54. Each imaging unit 50, 52, 54 comprises an imaging element 56, 58 and 60 respectively, mounted in the shaft 30 at the distal end 32. The imaging elements 56, 58, 60 may preferably have an identical configuration and are for example in the form of lenses.

The imaging elements 56, 58, 60 are arranged in a planar arrangement in relation to one another at the distal end 32 of the shaft 30, wherein axes 62, 64 and 66 respectively defined thereby run parallel to one another and parallel to an axis 68 defined by the shaft 30. The planes of lenses of the imaging elements 56, 58 and 60 coincide.

Figure 3:
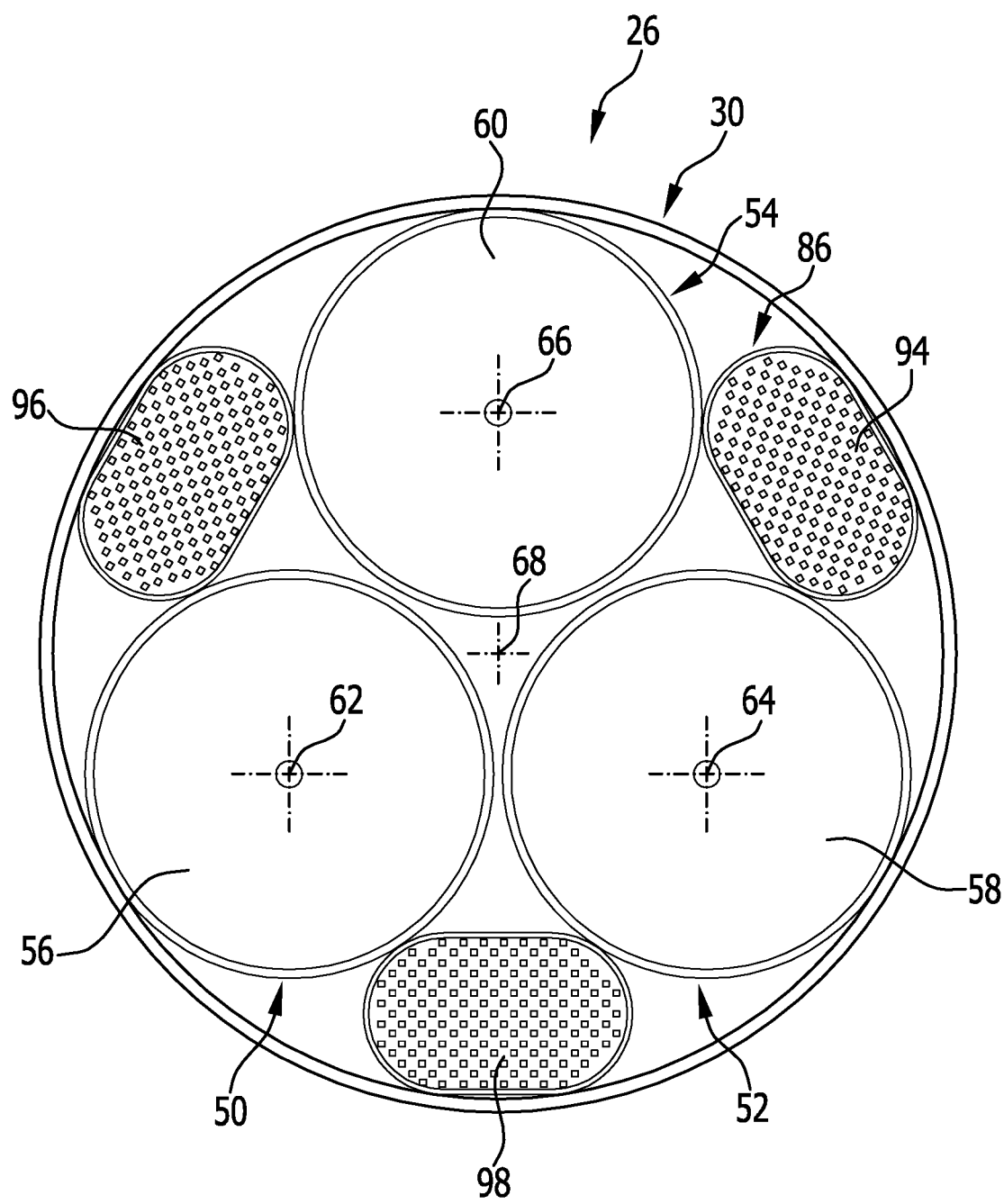
FIG. 3 shows an illustration of a distal end of the shaft of an endoscope of the device, in the direction of the arrow "A" in FIG. 2.

The imaging elements 56, 58 and 60 are positioned on the shaft 30 symmetrically in relation to one another, in an equilateral triangle (FIG. 3, viewing the distal end 32 of the shaft 30 axially in the proximal direction).

Each imaging element 56, 58 and 60 defines a field of view (not illustrated in the drawing) in which regions of the abdominal cavity 22 and in particular the organ 20 may be arranged. Objects in the respective field of view of an imaging element 56, 58, 60 are imaged on image sensors 70, 72 and 74 respectively of the imaging units 50, 52 and 54 respectively. A respective image sensor 70, 72 and 74 is associated with each imaging element 56, 58, 60 (that is to say 56 goes with 70, 58 with 72 and 60 with 74).

Light collected by the imaging elements 56, 58, 60 is guided, by light conducting elements (not illustrated in the drawing) that are guided in the shaft 30, to the housing 34 of the handle element 28, in which the image sensors 70, 72, 74 are arranged. Further imaging elements (not shown) may be provided in order to image light on a respective one of the image sensors 70, 72, 74.

In another kind of advantageous embodiment, it may be provided for image sensors to be positioned directly in the shaft 30, for example directly proximal in respect of the imaging elements 56, 58, 60, as a result of which light conducting elements may be dispensed with.

The image sensors 70, 72, 74 are coupled to the evaluation unit 42 by way of a signal line 76. A respective image data set 78, 80 and 82, each provided by one image sensor 70, 72, 74, may be preprocessed by an evaluation member 84 of the evaluation unit 42 (illustrated schematically in FIG. 2). The image data sets 78, 80 and 82 and/or preprocessed information may be supplied to a processing member 85 of the processor unit 44.

As a whole, because of the configuration and programming of the data processing unit 36, it is possible to analyze the image data sets 78, 80 and 82 of the image sensors 70, 72 and 74 respectively.

The device 10 comprises an illuminating unit 86 for illuminating the scene in the interior of the body, in order to improve the imaging properties of the device 10. The illuminating unit 86 comprises a light source 88, which in the present case is received in a housing 90 outside the endoscope 26. A light guide 92 is guided from the housing 90 to the housing 34 of the endoscope 26. Coupled to the light guide 92 are three illuminating elements 94, 96 and 98, which in the present case take the form of light conducting elements in the form of optical fiber bundles.

The illuminating elements 94, 96, 98 are guided from the housing 34 through the shaft 30 and extend as far as the distal end 32.

At least in the region of the distal end 32, the illuminating elements 94, 96, 98 are arranged symmetrically in relation to one another in an equilateral triangle (in relation to a proximal direction of view of the distal end 32). Further, there is a symmetry in the arrangement of the illuminating elements 94, 96, 98 in relation to the imaging elements 56, 58 and 60. Each illuminating element 94, 96, 98 is arranged diametrically opposite one of the imaging elements 56, 58 and 60 respectively in relation to the axis 68 of the shaft 30.

In this way, as even as possible an illumination of the scene in the interior of the body is made possible. The arrangement of the illuminating elements 94, 96, 98 distally and radially to the outside of the imaging elements 56, 58 and 60 proves advantageous for the purpose of avoiding reflections at the at the objects to be displayed.

Figure 4:
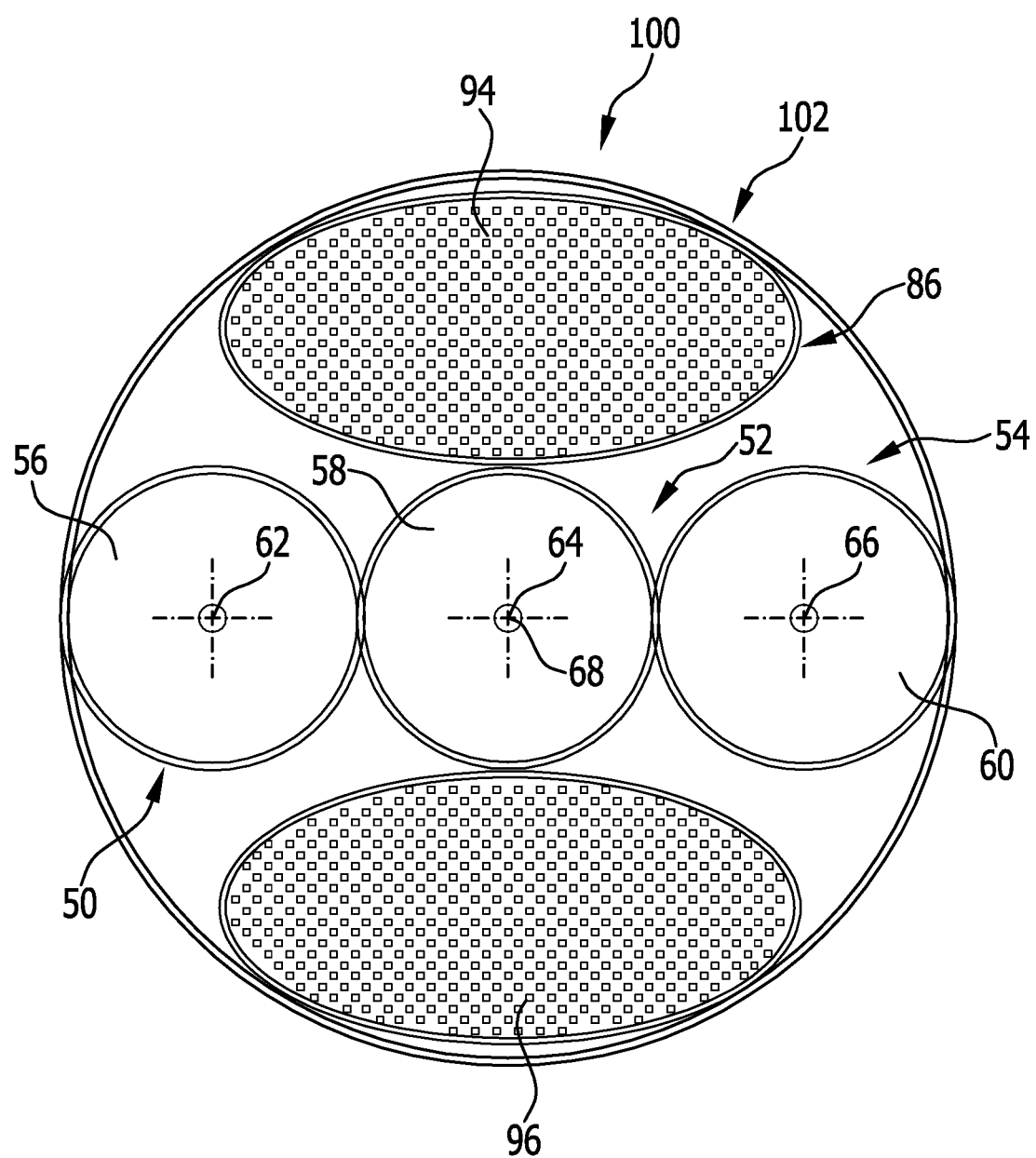
FIG. 4 shows an illustration in accordance with FIG. 3, in a different kind of configuration of the endoscope.

In another kind of advantageous embodiment of a device in accordance with the invention, an endoscope 100 that takes a different form from the endoscope 26 may be provided, the shaft 102 whereof is illustrated in FIG. 4 in a manner corresponding to FIG. 3.

In the case of the endoscope 100, the imaging elements 56, 58, 60 are positioned collinearly, wherein the axes 62, 64 and 66 respectively thereof run parallel to one another. The axis of the center imaging element coincides with the axis 68 of the shaft 102.

In the differently formed device, the illuminating unit 86 comprises two illuminating elements 94, 96, which are positioned laterally next to the triple arrangement of the imaging elements 56, 58 and 60.

As already explained, the image sensors 70, 72 and 74 may take different forms. For example, the image sensors 70 and 72 are configured to be identical, as monochrome sensors, and in particular as grayscale sensors. The image sensors 70, 72 may accordingly achieve a comparatively high resolution.

In the case of the device 10, the image sensor 74 may differ from the image sensors 70, 72 in respect of its resolution and/or spectral sensitivity. In the present case, the image sensor 74 is for example a color image sensor for color image representation, for example in RGB format.

The data processing unit 36 is configured and programmed such that it generates a stereo image 104 from the image data sets 78, 80 of the image sensors 70 and 72 respectively. The stereo image 104 may be represented on the display unit 46, and shows the surgeon 24 the scene in the abdominal cavity 22, in order to facilitate guiding of the endoscope 26 for him or her.

Moreover, the data processing unit 36 is configured and programmed such that it analyzes the image data sets 78, 80 and 82 for corresponding (so-called homologous) image points, and identifies corresponding image points in the image data sets 78, 80 and 82. In this way, it is possible for the data processing unit 36 to eliminate with a high level of precision any ambiguities that may occur in the case of only two image data sets by taking into account a third image data set.

Using the image data sets 78, 80 and 82, the data processing unit 36 can generate a 3D surface data set of imaged objects, for example the organ 20. A 3D image 106 of the 3D data set can be represented on the display unit 46. It is also possible to overlay the 3D image 106 with the stereo image 104.

The analysis of the image data sets 78, 80 and 82 may in particular be performed in real time, at intervals of less than a second. The continuous analysis of the image data sets 78, 80, 82 makes it possible for the data processing unit 36 to determine changes in the position and/or shape in the organ 20 as a function of time. The organ 20 can accordingly be tracked by the data processing unit 36, wherein the surface of the organ 20 is reconstructed almost in real time as a result of the continuous analysis in each case of the image data sets 78, 80, 82. This drastically enhances the usefulness and user-friendliness of the device 10 for the surgeon 24. In particular, the surgeon 24 has available additional information that is not available in the case of conventional endoscopic devices.

When the three imaging units 50, 52 and 54 are taken into account, it is possible to overcome difficulties that occur when conventional technology for display, including stereo display, is used in the medical environment. As already mentioned, ambiguities may largely be eliminated. This makes it possible to reconstruct the surface of regions of the organ 20 that are homogeneous or lacking in texture. Reflections at the examined organ 20 are less disruptive, since the additional image information facilitates the search for corresponding image points in the image data sets 78, 80 and 82.

Moreover, as a result of integrating all the imaging elements 56, 58 and 60 and additionally the illuminating elements 94, 96 and 98 in the same shaft 30, a very compact overall form is produced. It is possible to examine the patient 18 with a low level of invasiveness.

Further, the device 10 can have at least one tool 108, which in the present case takes the form of a surgical instrument 110. A coding 112 may be provided on the instrument 110. In the present case, the coding 112 comprises a plurality of coaxial rings 114 that are arranged at an axial spacing from one another on a shaft 116 of the instrument 110.

The data processing unit 36 can identify the instrument 110 from the coding 112 and, as with the organ 20, track it as a viewed object.

LIST OF REFERENCE NUMERALS

10 Device
12 Subject under examination
14 Object
16 Body
18 Patient
20 Organ
22 Abdominal cavity
24 Surgeon
26 Endoscope
28 Handle element
30 Shaft
32 Distal end 34 Housing
36 Data processing unit
38 Housing
40 Housing
42 Evaluation unit
44 Processor unit
46 Display unit
48 Image display
50, 52, 54 Imaging unit
56, 58, 60 Imaging element
62, 64, 66 Axis
68 Axis
70, 72, 74 Image sensor
76 Signal line
78, 80, 82 Image data set
84 Evaluation member
85 Processing member
86 Illuminating unit
88 Light source
90 Housing
92 Light guide
94, 96, 98 Illuminating element
100 Endoscope
102 Shaft
104 Stereo image
106 3D image
108 Tool
110 Instrument
112 Coding
114 Ring
116 Shaft

What is claimed is:

1. An endoscopic device, comprising:
an endoscope with a shaft that is introducible into a subject under examination,
a data processing unit, and
three or more optical imaging units comprising respective imaging elements arranged distally on the shaft and respective image sensors associated therewith for providing three or more image data sets for the data processing unit,
wherein the data processing unit is configured and programmed to:
analyze each of the three or more image data sets and determine corresponding image points in each of the three or more image data sets;
on the basis of the three or more image data sets, generate a 3D surface data set of an object in the subject under examination imaged by the three or more optical imaging units;
identify the object in the respective 3D surface data set and determine differences between successive 3D surface data sets; and
determine changes in a position and/or shape of the object in the successive 3D surface data sets as a function of time so as to track the object, at least in sections thereof.

2. The device in accordance with claim 1, wherein the data processing unit determines the corresponding image points for generating the 3D data set in real time.

3. The device in accordance with claim 1, wherein the data processing unit uses two image data sets from the three or more image data sets to generate a stereo image data set, which is examined for corresponding image points in at least one further image data set.

4. The device in accordance with claim 1, wherein the data processing unit generates from each combination of two image data sets derived from the three or more image data sets respective stereo image data sets, each of which is examined for corresponding image points in a respective further image data set.

5. The device in accordance with claim 1, further comprising a display unit coupled to the data processing unit and at least one of:
the data processing unit uses two image data sets to generate a stereo image of the object and represents it on the display unit;
the data processing unit represents an image of the 3D data set on the display unit.

6. The device in accordance with claim 1, wherein the imaging elements are arranged collinearly on the shaft or wherein one of the imaging elements is arranged on the shaft symmetrically in relation to a base formed by two further imaging elements.

7. The device in accordance with claim 1, wherein the imaging elements are arranged in a regular arrangement on the shaft, for example in an isosceles or in an equilateral triangle.

8. The device in accordance with claim 1, wherein at least two imaging elements are arranged in a planar arrangement with one another.

9. The device in accordance with claim 1, wherein the image sensors are arranged in the shaft and are coupled by way of signal lines to the data processing unit, which is positioned outside the subject under examination, or wherein the imaging elements are coupled, by way of light conducting elements guided in the shaft, to the image sensors, which are arranged in a housing, outside the subject under examination.

10. The device in accordance with claim 1, further comprising an illuminating unit having at least one illuminating element that is introducible into the subject under examination.

11. The device in accordance with claim 10, wherein a plurality of illuminating elements is provided.

12. The device in accordance with claim 11, wherein a respective illuminating element is associated with a corresponding imaging unit.

13. The device in accordance claim 10, wherein the illuminating element comprises or forms at least one light conductor guided in the shaft.

14. The device in accordance with claim 13, wherein the light conductors are arranged at least one of symmetrically to one another and symmetrically in relation to the imaging elements in the shaft.

15. The device in accordance with claim 14, wherein the light conductors are arranged radially to an outside of the imaging elements in relation to an axis of the shaft.

16. The device in accordance with claim 1, wherein the shaft is rigid or flexible.

17. The device in accordance with claim 1, wherein at least one of:
at least two of the three or more image sensors differ from one another in respect of at least one of their spectral sensitivity and their resolution;
the spectral sensitivity of at least one image sensor lies in the infrared range, the range of the visible spectrum, or the ultraviolet range;
at least two of the three or more image sensors have an identical configuration in respect of at least one of their resolution and their spectral sensitivity;
two image sensors are monochrome sensors and a third image sensor is a color image sensor; and at least one image sensor is or comprises a time-of-flight sensor that provides a distance image data set, wherein the data processing unit uses the distance image data set to determine an item of distance information for the purpose of comparison with a stereo image data set obtained from other image data sets.

18. The device in accordance with claim 1, wherein at least one of:
- using the data processing unit, monitoring of the imaging properties of the imaging units is performable and, in the event of a discrepancy from one of a setpoint conditions, a nominal condition, and a target state of the imaging properties, an indication regarding this discrepancy is output; and
- the device has at least one tool for the purpose of manipulation in the subject under examination, wherein the tool comprises a coding, which is detectable in the image data sets by the data processing unit for the purpose of identifying the tool.

19. The device in accordance with claim 1, wherein at least two image sensors are arranged in a planar arrangement with one another.

20. A method for the endoscopic examination of a subject under examination, comprising:
- introducing a shaft of an endoscope into a subject under examination,
- imaging an object in the subject under examination,
- wherein three or more optical imaging units comprising respective imaging elements that are arranged distally on the shaft and respective image sensors associated therewith are provided for the purpose of providing three or more image data sets for the data processing unit,
- wherein the data processing unit is configured and programmed to:
  - analyze each of the three or more image data sets and determine corresponding image points in each of the three or more image data sets;
  - on the basis of the three or more image data sets, generate a 3D surface data set of an object in the subject under examination imaged by the three or more optical imaging units;
  - identify the object in the respective 3D surface data set and determine differences between successive 3D surface data sets; and
  - determine changes in a position and/or shape of the object in the successive 3D surface data sets as a function of time so as to track the object, at least in sections thereof.

* * * * *